(12) United States Patent
Aas et al.

(10) Patent No.: US 8,728,288 B2
(45) Date of Patent: May 20, 2014

(54) SENSOR ASSEMBLY

(75) Inventors: Flemming Aas, Dyssegard (DK); Erik Helleso Nicolajsen, Copenhagen (DK)

(73) Assignee: Radiometer Medical Aps (DK)

( * ) Notice: Subject to any disclaimer, the term of this patent is extended or adjusted under 35 U.S.C. 154(b) by 1265 days.

(21) Appl. No.: 12/081,997

(22) Filed: Apr. 24, 2008

(65) Prior Publication Data

US 2009/0060789 A1 Mar. 5, 2009

(30) Foreign Application Priority Data

Apr. 27, 2007 (EP) .................................... 07388028

(51) Int. Cl.
*G01N 27/00* (2006.01)
*B01L 3/00* (2006.01)

(52) U.S. Cl.
USPC ........ 204/411; 204/400; 204/409; 422/82.01; 422/82.02; 422/502; 422/503; 436/43; 436/149; 436/150

(58) Field of Classification Search
USPC ............... 204/193, 194, 400, 403.01, 403.03, 204/403.13, 412; 422/68.1, 82.01–82.04; 436/43, 149, 150
See application file for complete search history.

(56) References Cited

U.S. PATENT DOCUMENTS

| 5,520,787 | A | * | 5/1996 | Hanagan et al. ......... 204/403.14 |
| 5,858,452 | A | | 1/1999 | Leader et al. |
| 6,123,820 | A | | 9/2000 | Bergkuist et al. |
| 6,207,369 | B1 | * | 3/2001 | Wohlstadter et al. ........ 435/6.11 |
| 6,331,438 | B1 | | 12/2001 | Aylott et al. |
| 2002/0142477 | A1 | | 10/2002 | Lewis et al. |

FOREIGN PATENT DOCUMENTS

| EP | 1 362 827 A1 | 11/2003 |
| JP | 2003-515163 A | 4/2003 |

\* cited by examiner

*Primary Examiner* — Paul Hyun
*Assistant Examiner* — Robert Eom
(74) *Attorney, Agent, or Firm* — Finnegan, Henderson, Farabow, Garrett & Dunner LLP

(57) ABSTRACT

The invention relates to a sensor assembly comprising a first electronic wiring substrate having a first and a second surface and at least one analyte sensor formed on the first surface thereof, the at least one analyte sensor being connected with one or more electrical contact points, a second electronic wiring substrate having a first and a second surface and at least one analyte sensor formed on the first surface part thereof, the at least one analyte sensor being connected with one or more electrical contact points, and a spacer having a through-going recess with a first and a second opening, wherein the first substrate, the second substrate and the spacer are arranged in a layered structure, where the first surface of the first substrate closes the first opening of the spacer and the first surface of the second substrate closes the second opening of the spacer, thereby forming a measuring cell which is faced by at least one sensor from each of the substrates.

13 Claims, 8 Drawing Sheets

SENSOR ASSEMBLY

Figure 1:
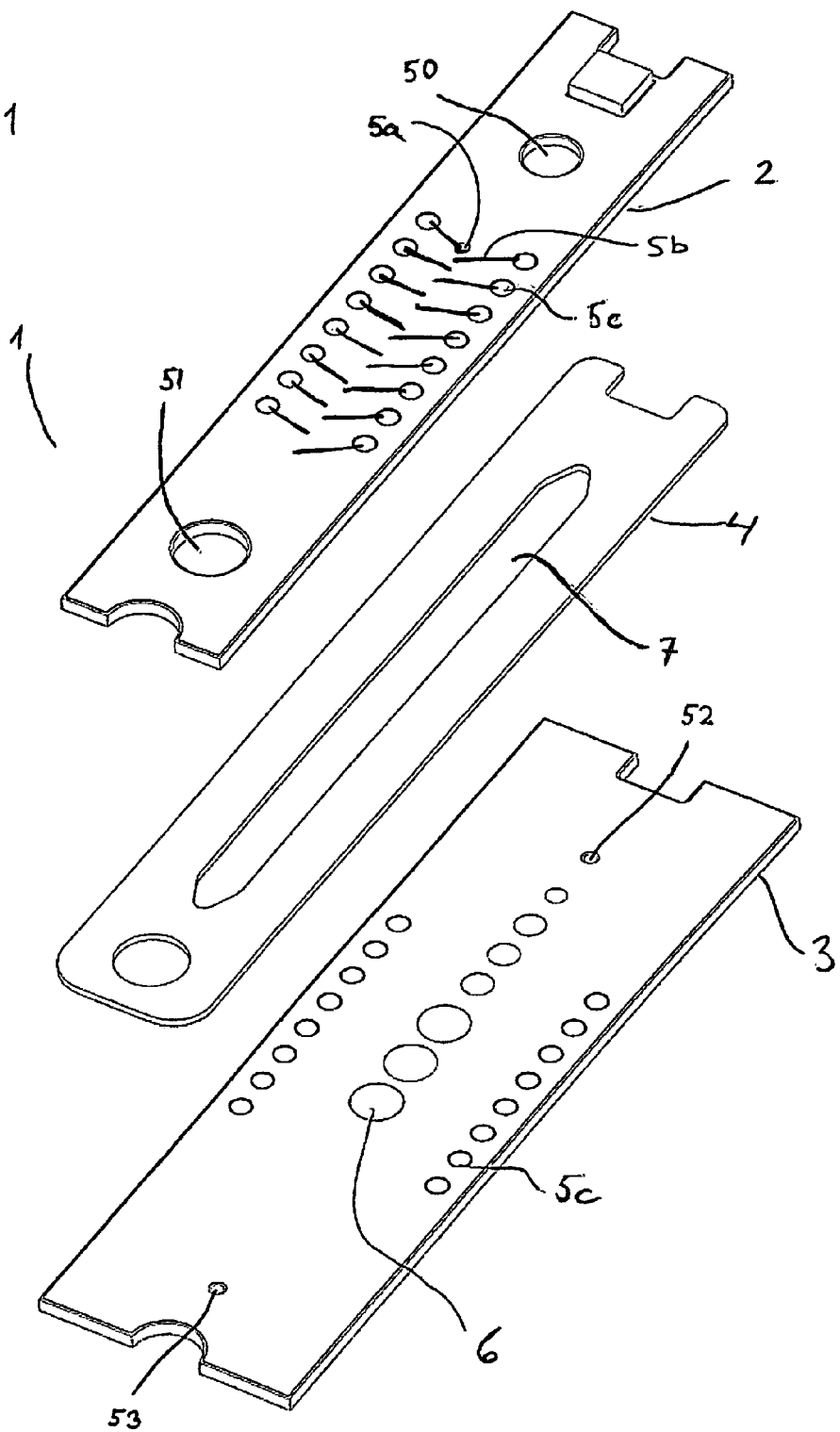

The present invention relates to a sensor assembly, in particular a sensor assembly comprising electrochemical sensor elements. The sensor assembly of the present invention is particularly suitable for simultaneously measuring a plurality of different parameters, e.g. blood parameters.

In a variety of instances it is desirable to measure e.g. the partial pressure of blood gasses in a whole blood sample, concentrations of electrolytes and metabolites in the blood sample, as well as the hematocrit value of the blood sample. For example, measuring $pCO_2$, $pO_2$, pH, $Na^+$, $K^+$, $Ca^{2+}$, $Cl^-$, glucose, lactate and hemoglobin values are primary clinical indications in assessing the condition of a medical patient. A number of different analyzers currently exists for making such measurements. Such analyzers are able to perform precise measurements in order to provide the most meaningful diagnostic information. In addition, in an attempt to use as little of the patient's blood as possible in each analysis performed, the measuring cell which is employed to analyze a blood sample are preferably relatively small. Performing blood analysis using a small blood sample is important when a relatively large number of samples must be taken in a relatively short amount of time or if the volume of blood is limited, as in neonates. For example, patients in intensive care require a sampling frequency of 15-20 per day for blood gas and clinical chemistry measurements, leading to a potentially large loss of blood during patient assessment. Furthermore, in order to limit the number of tests which must be performed it is desirable to gather as much information as possible upon completion of each test. However, size limitations are imposed upon the sensors that are used to measure blood chemistry. These size limitations are in large part due to physical geometries of the sensors and the connections to the sensors.

One attempt to solve this problem is found in U.S. Pat. No. 5,916,425, which discloses an electronic wiring substrate for sensors formed over a subminiature through hole. The small diameter of the through hole allows a relatively large number of sensors to be formed on the surface of the substrate within a relatively small fluid flow cell. Thus, more information may be attained using less blood. In addition, the sensors disclosed in U.S. Pat. No. 5,916,425 may be fabricated in small areas, allowing a relatively large number of sensors to be deposited in a small flow cell.

U.S. Pat. No. 6,123,820 discloses sensor a cartridge including several sensors. The disclosed sensor cartridge comprises two sensor boards. The sensor boards are plate-like and have two major surfaces, where one of the major surfaces carries several sensors. The two sensor boards face an intermediate part having a zig-zag flow channel providing a series of sensor ports on both sides of the intermediate part in such a way that each sensor on the two sensor boards is facing a sensor port to form a measuring cell. A number of individual measuring cells are connected by flow channel segments formed in the intermediate part. The sensor cartridges tends to reduce the required size of the sample, however, the individual measuring cells connected through flow channel segments do require a certain size of the sample. Moreover, contamination may flow from one measuring cell to the next and accumulate in the sample flowing through the flow channel. The sensor cartridge is relatively complicated to produce, partly due to the zig-zag configuration of the flow channel in the intermediate part.

Although the above-mentioned sensors partially meet the requirement for measurements with smaller samples there is still a demand for sensor assemblies capable of performing precise and fast measurements on even smaller sample sizes.

It is an object of the present invention to provide a system with a very compact sensor assembly that requires only a minimum amount of sample fluid for precise measurement.

Consequently, as an alternative to the prior art sensors, the invention provides a sensor assembly in which several analyte sensors in a very small volume may be positioned in contact with a sample. The sensor assembly is able to measure several parameters on the small sample volume.

Furthermore, the invention provides a sensor assembly in which a smaller sample volume may be used than in similar prior art sensor assemblies without reducing the number of sensors in the sensor assembly. Moreover, it has surprisingly appeared that it is possible to have fully functional sensor elements placed on opposing walls in a measuring cell.

According to a first aspect of the invention the above object and other objects are fulfilled by providing a sensor assembly comprising:

- a first electronic wiring substrate having a first and a second surface and at least one analyte sensor formed on the first surface thereof, the at least one analyte sensor being connected with one or more electrical contact points,
- a second electronic wiring substrate having a first and a second surface and at least one analyte sensor formed on the first surface part thereof, the at least one analyte sensor being connected with one or more electrical contact points, and
- a spacer having a through-going recess with a first and a second opening, wherein the first substrate, the second substrate and the spacer are arranged in a layered structure, where the first surface of the first substrate closes the first opening of the spacer and the first surface of the second substrate closes the second opening of the spacer, thereby forming a measuring cell which is faced by at least one sensor from each of the substrates.

In general a measuring cell is a cell in which a sample is kept during measurement on the sample. A measuring cell has at least one opening for bringing the sample into contact with an analyte sensor.

It has unexpected appeared that it is possible to measure two or more parameters in the same measuring cell, without any significant interference between opposing analyte sensors, although no walls, channels or the like are present to keep the analyte sensors separated. In most cases the analyte sensors on opposing surfaces in the measuring cell may be placed facing each other or offset to each other as desired.

In a preferred embodiment of the sensor assembly the measuring cell is faced by at least two sensors from one of the substrates. In a further preferred embodiment of the sensor assembly the measuring cell is faced by at least two sensors from each of the substrates. More preferable at least three or more sensors from each of the substrates is facing the measuring cell. The embodiments make it possible to obtain a measuring cell in which a large number of parameter values can be achieved on a very small sample.

The substrate is preferably a plate-like or rectangular sheet-like substrate capable of carrying the necessary wiring for connecting the analyte sensors with the electrical contact points. The first surface and the opposing second surface are of course the two major surfaces of the plate or sheet and preferably parallel. The spacing between the first surface and the second surface of the substrate defines the thickness of the substrate. The substrate as such is preferably a non-conductive material and the wiring is a conductive material like copper, silver, gold, platinum or conductive polymer.

Examples of such substrates with analyte sensors may be found in e.g. U.S. Pat. No. 5,916,425.

The spacing between the first substrate and the second substrate is defined by the thickness of the spacer. The measuring cell defined by the through-going recess in the spacer and the first surfaces of the substrates may be a closed cell, however, the measuring cell is preferably provided with an inlet and an outlet for conducting a fluid sample into and away from the measuring cell. In one embodiment two or more measuring cells, each comprising at least two opposing analyte sensors, may be connected in series via suitable connection devices such as channels. The fluid sample to be received is preferably a liquid sample, but it may, alternatively, be a gaseous sample, e.g. expired air. A liquid sample may advantageously be a sample of a body fluid, such as a blood sample, a urine sample, saliva etc., to be analyzed.

In a preferred embodiment the analyte sensors are blood parameter sensors. The analyte sensors may preferably be adapted to measure one or more of the following parameters: $pCO_2$, $PO_2$, pH, $Na^+$, $K^+$, $Ca^{2+}$, $Cl^-$, glucose, lactate, urea, and creatinine. Further parameters like bilirubin and hemoglobin values, such as $FO_2Hb$, $FCOHb$, $FMetHb$, $FHHb$ and $FHbF$, may be measured in an additional module. Alternatively, one or more of the analyte sensors may be adapted to measure parameters of other possible body fluids, such as urine, saliva and expired air.

When the sensor assembly is adapted to function in connection with a blood analyzer, the analyte sensors on the first substrate are preferably, in the flow direction, an optical sensor for measuring $PO_2$ followed by sensors of the thick film type for measuring potassium, sodium, pH and $pCO_2$ and optional a part of a creatinine sensor. A reference electrode is preferably also placed on the first substrate. The analyte sensors on the second substrate are preferably, in the flow direction, sensors of the thick film type for measuring chloride, magnesium, calcium, optionally urea, glucose, lactate and optionally a part of a creatinine sensor.

The first substrate and the second substrate are arranged opposite each other with the spacer part there between in such a manner that the recess is arranged in a position corresponding to the position of the analyte sensors of the first substrate as well as the position of the analyte sensors of the second substrate, each of the analyte sensors will thereby be facing the measuring cell. The analyte sensors will, thus, be able to measure parameter values on a fluid sample positioned in the measuring cell. The analyte sensors may be in direct fluid contact with the fluid sample. However, it may also be envisaged that a barrier, e.g. in the form of a thin membrane, sheet or foil, is positioned between the fluid sample and one or more of the analyte sensors, such analyte sensor(s) thereby being in indirect contact with the fluid sample.

Since the analyte sensors are arranged on the first surface of the first substrate as well as on the first surface of the second substrate and in direct or indirect contact with the measuring cell, and thereby with a fluid sample positioned therein, a very large number of analyte sensors are able to measure parameter values on the fluid sample at least substantially simultaneously. Thus, the number of possible analyte sensors may be significantly increased without decreasing the size of the individual analyte sensor. Furthermore, if the size of the individual analyte sensor is additionally decreased, an even larger number of analyte sensors will be able to measure parameters of the fluid sample while maintaining a very small sample volume. Alternatively, the sample volume could be reduced while allowing the same number of analyte sensors to measure parameters of the fluid sample. Consequently, the invention provides several advantages.

It is preferred that the spacing between the individual analyte sensors on the same substrate and the spacing between an analyte sensor on the first substrate and an analyte sensor on the second substrate should have an extension sufficient to avoid interference between the different sensors.

The measuring cell may have a shape that allows a fluid flowing through the measuring cell to perform an at least substantially linear movement. According to this embodiment the measuring cell should not have any or only a limited number of bends and turns. By avoiding bends and turns in the measuring cell, rinsing and cleaning of the measuring cell is significantly facilitated and the risk of bubble formation is reduced. In a preferred embodiment the fluid connections between an analyzer and the measuring cell may be substantially perpendicular to the main direction of the flow in the measuring cell, i.e. perpendicular to the first surfaces of the substrates. This may provide certain advantages when the sensor assembly with the measuring cell is being connected with an analyzer. Consequently, in preferred embodiments the measuring cell has inlet and outlet ports, the ports being formed in the first substrate, or the ports being formed in the second substrate. In a particular preferred embodiment the inlet and outlet ports are formed in the second substrate. This provides the advantage that the sensor assembly may easily be fluidly connected to the analyzer, simply by pressing the sensor assembly onto connection tubes on the analyzer, thereby connecting the inlet and outlet port with the connection tubes.

In an alternative embodiment the optional fluid connections between an analyzer and the measuring cell may be substantially parallel to the flow direction through the measuring cell.

Each analyte sensor is connected to an associated electrical contact point arranged on the same substrate as the respective sensor element for establishing electrical contact between each analyte sensor and an analyzer. Thereby information relating to a specific measurement may be transferred from the relevant analyte sensor to the analyzer via the associated electrical contact point. It should be noted that in some cases an analyte sensor may be connected to two or more electrical contact points. This may, e.g., be the case if the analyte sensor is an electrochemical sensor comprising two or more electrodes. In this case each of the electrodes in the sensor may be connected to an electrical contact point.

In a preferred embodiment the electrical contact points of the first substrate are arranged on the second surface of the first substrate and the electrical contact points of the second substrate are arranged on the first surface of the second substrate. The extent of the second substrate is preferably somewhat larger than the extent of the first substrate. The second substrate may have a larger extent in transverse or longitudinally direction than the first substrate. Alternatively the second substrate has a larger extent in both transverse and longitudinally direction than the first substrate. The longitudinally and transverse directions are defined in respect of the flow direction in the measuring cell. Thereby, when the sensor assembly is assembled and the substrates arranged with the sensor elements facing the measuring cell a part of the first surface of the second substrate extends beyond the boundaries of the first substrate. The electrical contact points of the second substrate are positioned on this extending part of the first surface and the electrical contact points of the first substrate and the electrical contact points of the second substrate will, thus, according to this embodiment, face in the same direction. Consequently, it will be possible to gain contact to each of the electrical contact points of the first and second substrates using a single contact unit comprising a sufficient amount of corresponding electrical contact points facing in the same direction. This significantly simplifies the design of the connection to the analyzer, and it is therefore considered a highly advantageous solution.

In case the analyte sensors and the electrical contact points are positioned on the first surface, the connection between an analyte sensor and an associated electrical contact point may advantageously be provided by an electrically conducting path, e.g. a platinum path which has been printed onto the substrate. Alternatively, the platinum path is lead through a first hole or bore in the substrate to the second surface, and back to the first surface through a second hole or bore to a required position on this surface. In case the analyte sensors are positioned on the first surface and the contact points are positioned on the second surface, the connection between an analyte sensor and an associated electrical contact point may alternatively or additionally comprise a hole or a bore going through the substrate. The hole or bore is filled with an electrically conductive material, such as copper, silver, gold, platinum or electrically conductive polymers.

Although the substrates may be made from suitable materials such as glass or plastic material, it is preferred that least one of the substrates is made from a ceramic material, such as aluminum oxide, or ceramic material based on silicon or boron.

The spacer may be made from plastic, rubber, ceramic and preferably the spacer is made from acrylic or similar plastic material. The spacer and the substrates are assembled in a sealed manner to minimize leakage of sample from the measuring cell. This sealing may be obtained by choosing the spacer from a sealing material, but may also be obtained by separate sealing means positioned between the spacer and the substrates.

The measuring cell provided by the recess in the spacer and the first surfaces of the first and second substrates preferably provides a volume of about 25-45 µl, more preferably a volume of about 30-40 µl. With such a volume very small samples are required for measurement by the analyte sensors in the measuring cell. Preferably the dimensions of the spacer are within the ranges: length 20-60 mm, width 5-20 mm, and thickness 0.2-0.6 mm. The recess within the spacer may have the dimensions within the ranges: length 10-50 mm, width 1-5 mm, and depth 0.2-0.6 mm.

The dimensions of the first and second substrates and the spacer, and thus, the dimension of the sensor assembly may be adapted depending on the intended use. However, in a preferred embodiment the first substrate has dimensions within the ranges: length about 20-60 mm, width about 5-20 mm, and thickness about 0.3-0.8 mm.

The width and/or the length of the second substrate may be somewhat larger than the width and/or length of the first substrate. This is due to the fact that for some preferred embodiments it is preferred that the first surface of the second substrate projects over the edges of the spacer and first substrate in the sensor assembly. The second substrate preferably has dimensions within the ranges: length about 20-60 mm, width about 5-40 mm, and thickness 0.3-0.8 mm. The length and width of the second substrate may provide an extension beyond the edges of the first substrate and spacer in the range of about 4-20 mm.

The sensor assembly may further comprise a reference electrode adapted to provide an at least substantially fixed electrical reference potential to the sensor assembly. Such a reference electrode is very useful in case one or more of the analyte sensors are electrochemical sensors comprising only a single electrode, where the electrical potential of this electrode varies with the concentration of a specific substance in the fluid sample, and where the analyte sensor is intended to measure this concentration. In this case the difference between the electrical potential measured by the sensor and the reference potential provided by the reference electrode will be used as the measured value. Thereby any possible offset value of the measured electrical potential will be removed from the measurement, and it is thereby ensured that the measured value reflects the actual concentration of the substance in the sample.

The sensor assembly may further comprise a liquid chamber adapted to hold a reference electrolyte, said liquid chamber keeping the reference electrolyte separated from the reference electrode during storage. The liquid chamber may be operated to bring the reference electrolyte into contact with the reference electrode. The reference electrode is kept dry during storage, e.g. in order to prevent or reduce degradation of the analyte sensors in the sensor assembly because if the analyte sensors come into contact with the electrolyte a slow degradation of the sensors will start. When it is desired to use the reference electrode, the reference electrolyte in the liquid chamber is released, and the reference electrolyte is thereby brought into contact with the reference electrode. Due to the reference electrolyte the reference electrode is able to provide the at least substantially fixed electrical reference potential to the sensor assembly. To release the reference electrolyte the liquid chamber may be manually operable, e.g. by pushing a part of the sensor assembly. The liquid chamber may also be operable by the analyzer e.g. by a mechanical action. Preferably the reference electrolyte is released from the liquid chamber by the action of a valve arrangement or by the action of a rocking mechanism connected with a plug. In case a valve arrangement is used it is preferably a double valve system housing the reference electrolyte between the two valves and when the double valve system is pushed down the reference electrolyte is released. In case a rocking mechanism is employed the rocking mechanism will, when activated, remove a plug from a passage allowing release of the reference electrolyte to come into contact with the reference electrode.

The sensor assembly may be at least substantially enclosed in a housing. In this case the sensor assembly forms a unit defined by the outer boundaries of the housing, and it is thereby very easy to handle, e.g. during shipment, storage and use. It should be noted that in the present context the term 'housing' should be interpreted as an at least substantially closed part enclosing each of the other parts of the sensor assembly. The housing may be provided with at least substantially rigid and/or tight walls. However, it may alternatively or additionally comprise one or more soft walls and/or one or more grid-like walls, as long as the housing encloses the parts of the sensor assembly. In a preferred embodiment the sensor assembly is designed with finger-holding devices in order to make the sensor assembly easy to handle, e.g. when the sensor assembly is to be placed in or removed from an analyzer.

Accordingly there is provided a system for providing a ready-to-use sensor assembly to an analyzer, which system comprises a sensor assembly and conditioning unit and where the conditioning unit comprises a storage compartment for the sensor assembly. The storage compartment is connected with a liquid compartment containing a conditioning liquid that upon activation of the conditioning unit is transferred into the sensor assembly.

According to the system a sensor assembly may be stored in the conditioning unit under dry conditions. When it is desired to use the sensor assembly, a fluid connection is established and the conditioning liquid is allowed to enter the sensor assembly in the storage compartment. Thereby the sensor assembly may be conditioned before it is positioned in an analyzer and will be ready for use as soon as it is positioned in the analyzer. Thus, inoperable time of the analyzer is thereby reduced. The analyzer is preferably an analyzer for analyzing blood samples.

The liquid contained in the liquid compartment is preferably a liquid composed to condition the sensors in the sensor assembly, preferably composed to condition specific sensors present in the sensor assembly.

The storage compartment may preferably be adapted to accommodate a sensor assembly according to invention, i.e. it preferably has a size and a shape allowing such a sensor assembly to fit therein.

The means for establishing a fluid connection may be manually operable, e.g. by twisting, turning, pushing or pulling a part of the storage compartment or a part of the liquid compartment, or by activating a switch or a push button. Alternatively, the means for establishing a fluid connection may be operated in any other suitable manner, e.g. by means of a pressure or spring driven device.

Figure 2:
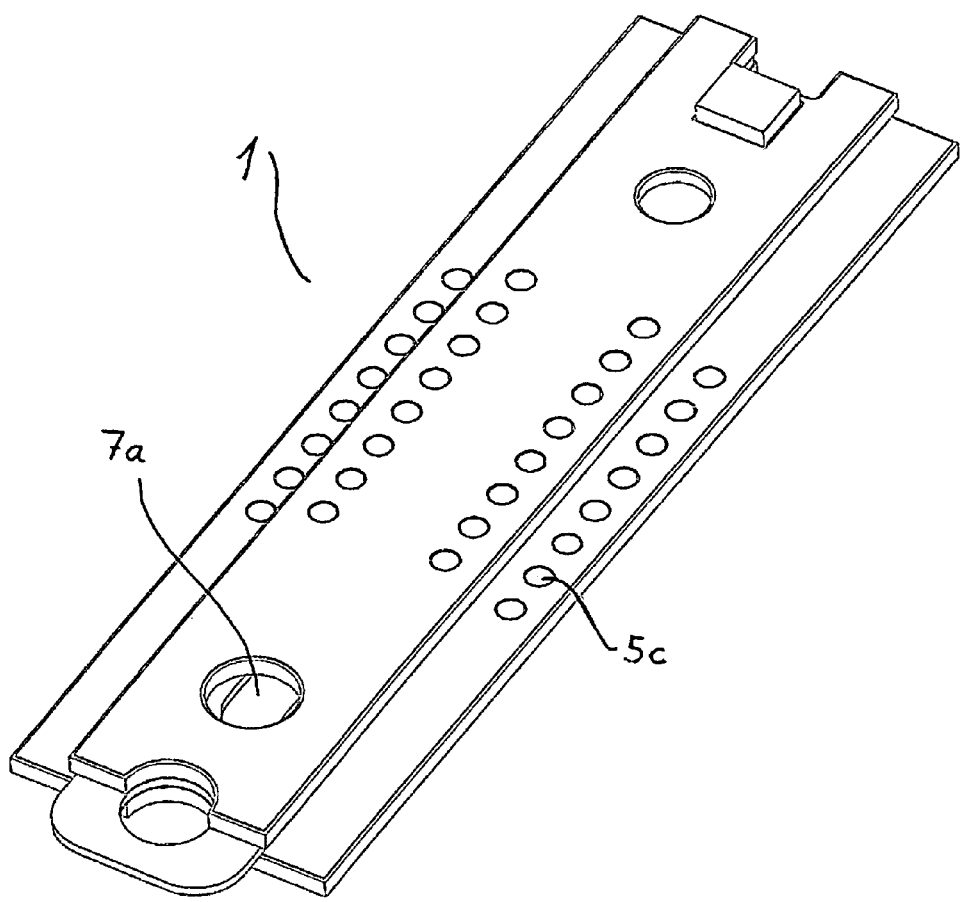
Figure 3:
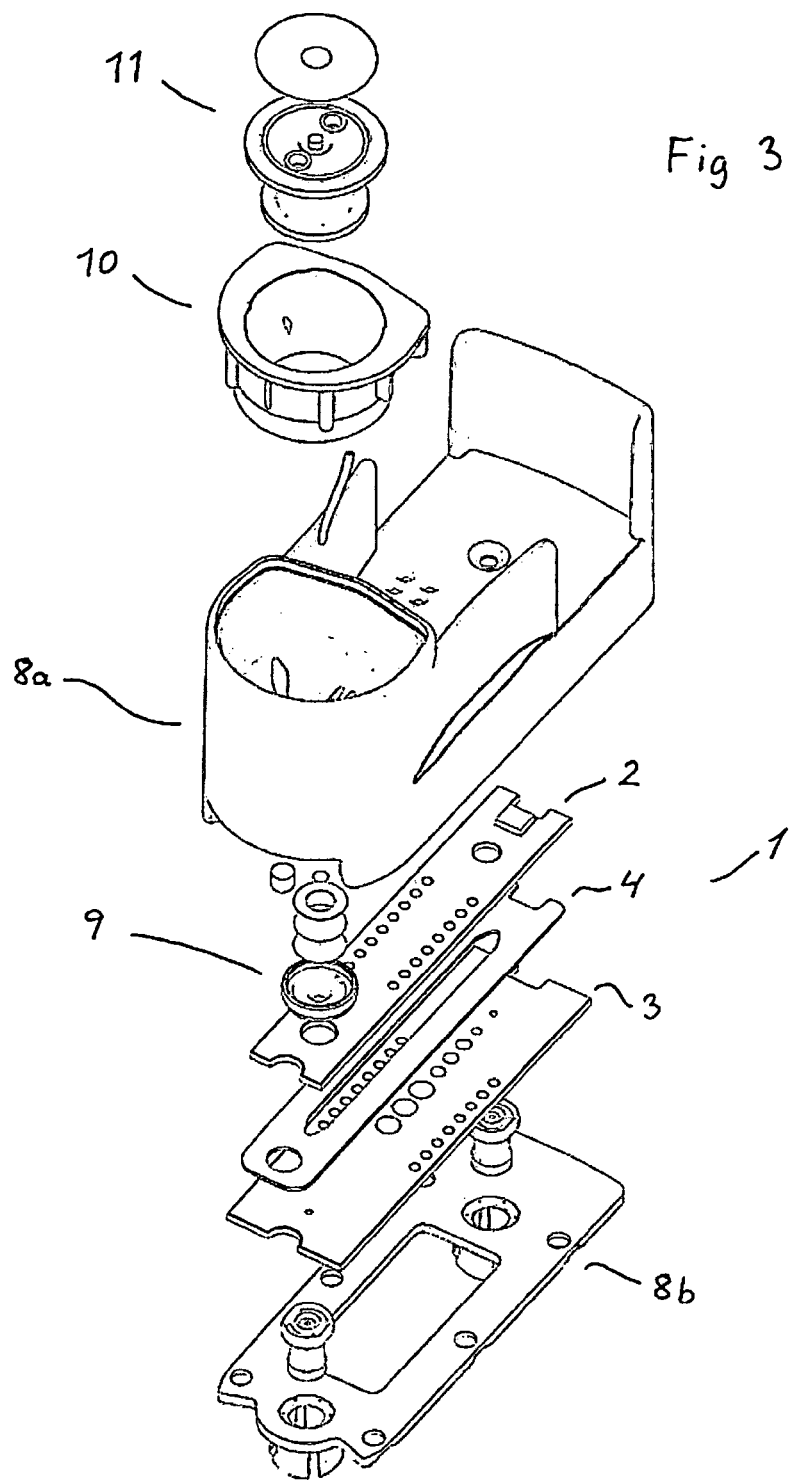
Figure 4:
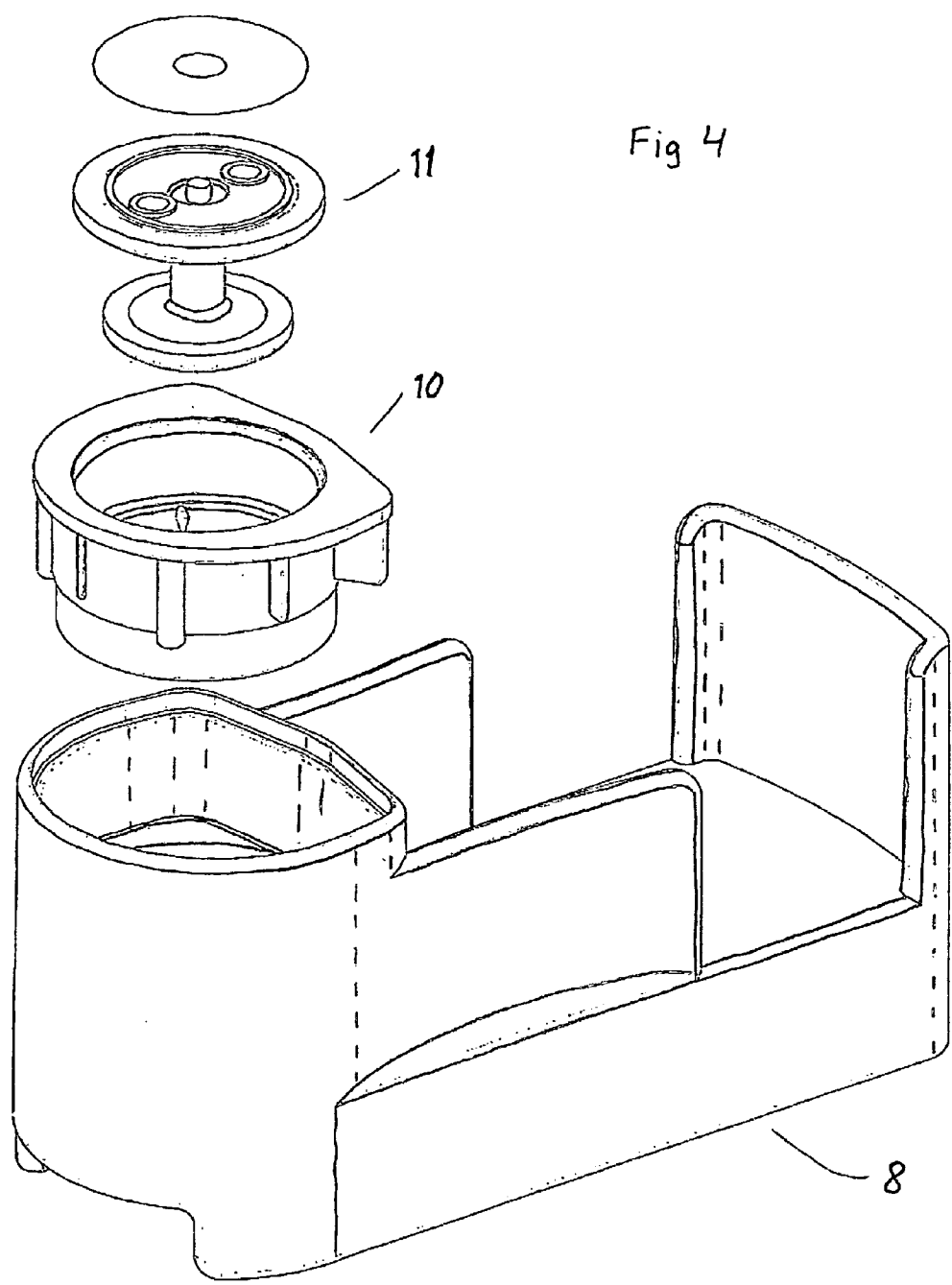
Figure 5:
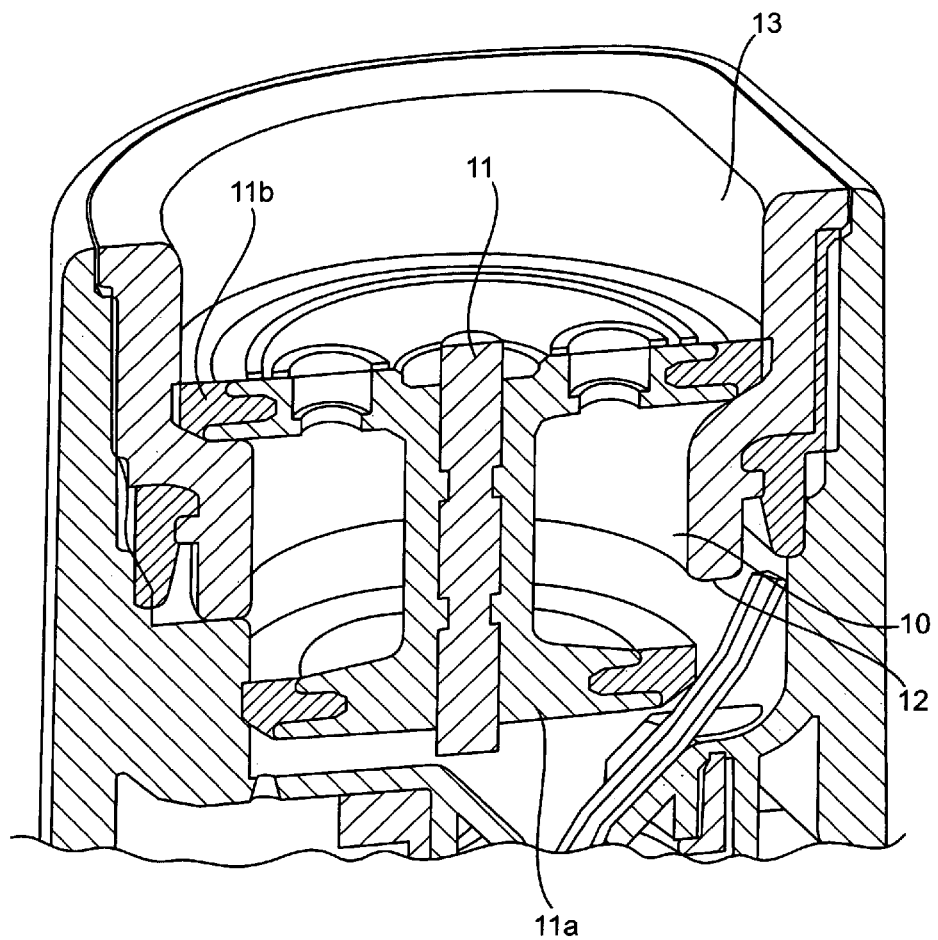
Figure 6:
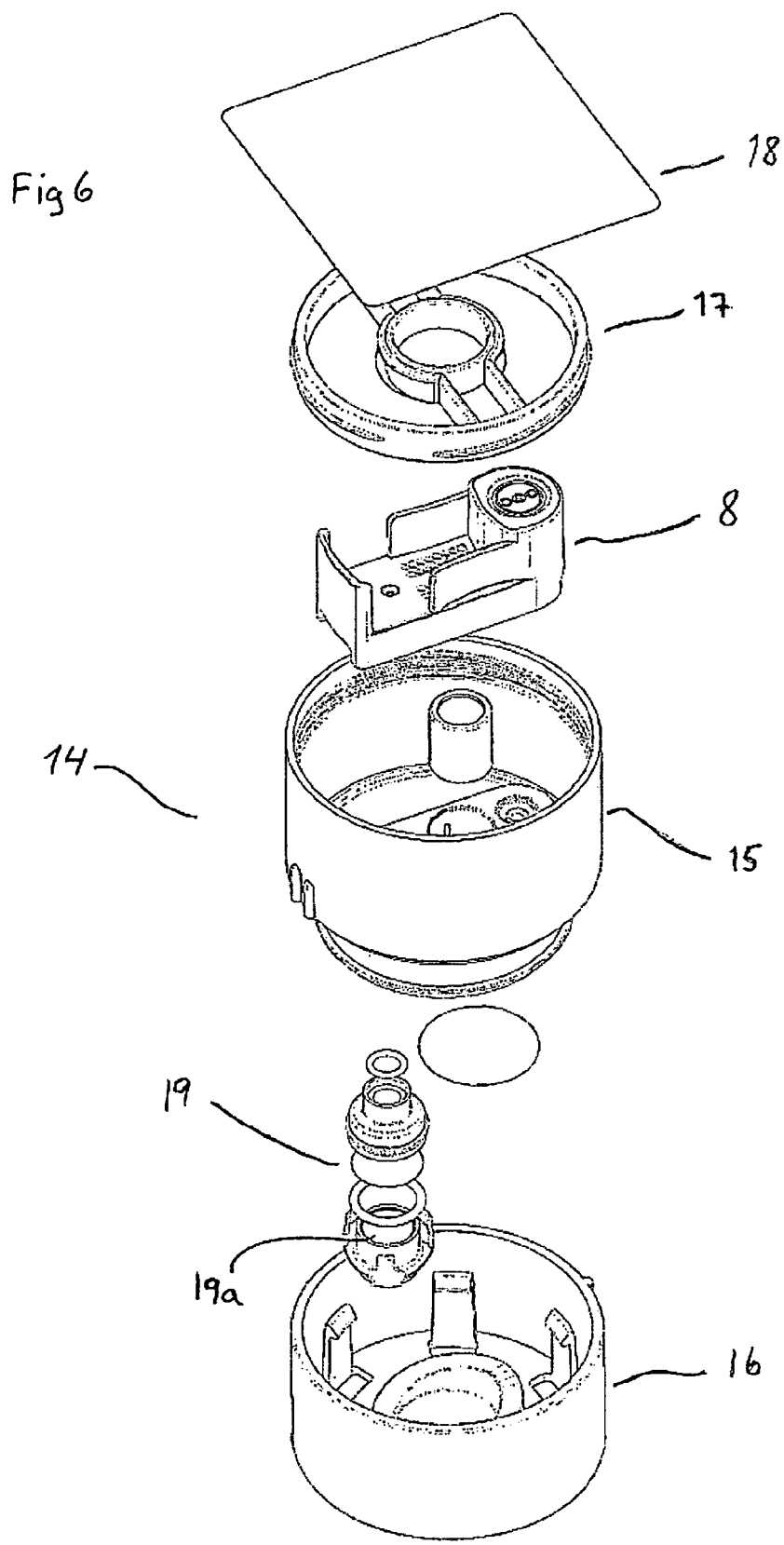
Figure 7:
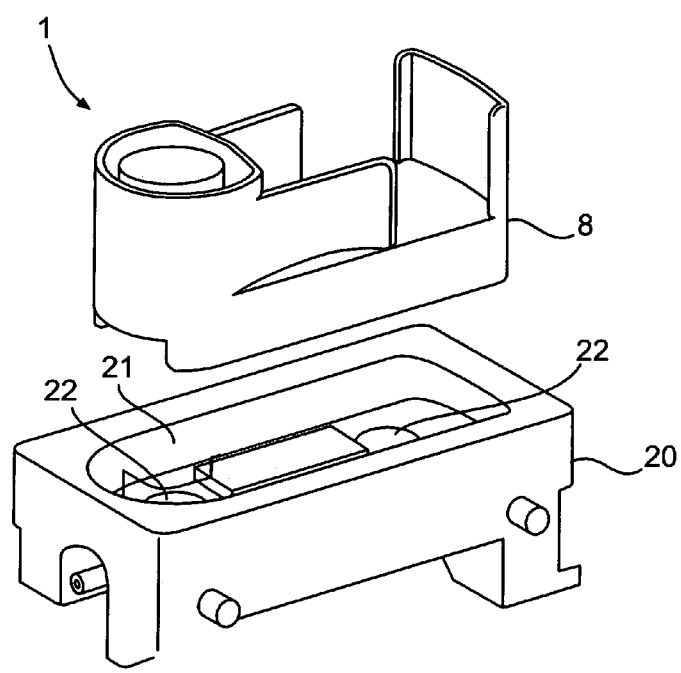
Figure 8:
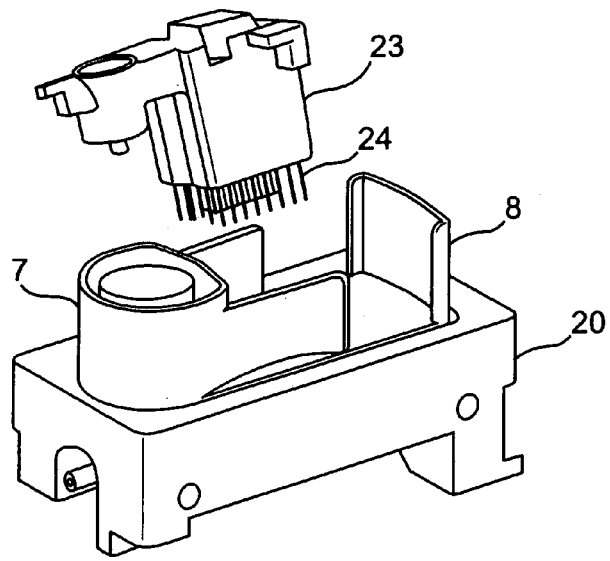
Figure 9:
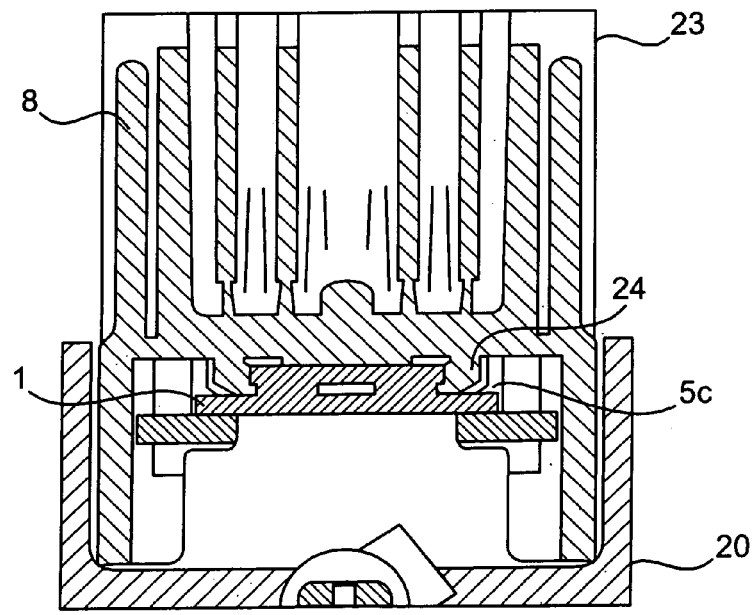

The invention will now be described in further details with reference to the accompanying drawings in which:

FIG. 1 is an exploded view of a sensor assembly according to an embodiment of the invention, FIG. 2 is a perspective view of the sensor assembly of FIG. 1, FIG. 3 is an exploded view of a sensor assembly of FIG. 1 enclosed in a housing, FIG. 4 is an exploded view of a liquid chamber for a reference electrode for the sensor assembly of FIG. 1, FIG. 5 is a cross sectional view of the liquid chamber of FIG. 4, FIG. 6 is an exploded view of a conditioning unit according to an embodiment of the invention, FIG. 7 is a perspective view of a sensor assembly comprising a housing adapted to connect with an analyzer, FIG. 8 is a perspective view of sensor assembly comprising a housing placed in a holder of an analyzer and a contact element, and FIG. 9 is a cross sectional view of the sensor assembly with the electric contact points in contact with the contact element. The sensor assembly comprising a housing is located in a holder of an analyzer.

The sensor assembly according to the invention and the conditioning unit may be used in bio mechanical engineering e.g. in apparatuses adapted for analyzing biological samples. Although the sensor assembly and conditioning unit may be useful in many applications within the field of analyzing samples, one preferred use is in connection with apparatuses designed to measure and analyze different parameters on a blood sample. Consequently, a sensor assembly according to the invention adapted for measuring on blood samples will be used as an example of the invention in this description.

In this description the term analyte sensor denotes any sensor capable of measuring a physical parameter, such as the concentration of a chemical substance. An analyte sensor may comprise one of more electrodes and one or more membranes.

An analyzer is to be understood as a device capable of receiving data from analyte sensors, e.g. as electrical signals, and to process such data and present the result of the processing. The analyzer also includes sensor assemblies and means for connecting the analyte sensors to the analyzer.

The electronic wiring substrate is a substrate made from ceramic material carrying wiring for connecting analyte sensors with an analyzer. The analyte sensors are preferably applied to the substrate by use of thick film technique.

FIG. 1 is an exploded view of a sensor assembly 1 comprising a first substrate 2, a second substrate 3 and a spacer 4.

The first substrate 2 is provided with a plurality of analyte sensors (not visible in the figure) arranged on a first surface of the first substrate and facing downward in the figure. The first substrate is furthermore provided with a plurality of electrical contact points 5c arranged on a second surface facing upwards in the figure. The electrical contact points 5c are connected to analyte sensors via wires 5b and tiny bores 5a in the sensor board. The bores 5a are filled with an electrical conductive material, e.g. platinum, which is connected to the analyte sensors on the first surface and the wire 5b on the second surface.

The second substrate 3 is also provided with a plurality of analyte sensors 6 and a plurality of electrical contact points 5c. The analyte sensors 6 as well as the electrical contact points 5c are arranged on a first surface of the second substrate 3 and facing upwards in the figure. The wiring between the analyte sensors 6 and the electrical contact points 5c on the second substrate is lead from the analyte sensors on the first surface to the second surface of the substrate 3 and back to the contacts points 5c on the first surface through holes in the substrate.

Although the embodiment of the sensor assembly shown in FIG. 1 discloses the substrates 2 and 3 provided with a plurality of analyte sensors, an alternative embodiment of the sensor assembly comprises a first substrate and a second substrate where the first substrate is provided with one analyte sensor and the second substrate is provided with one analyte sensor.

The spacer 4 is provided with a recess 7 in the form of an elongated bore extending through the major part of the spacer 4.

When the sensor assembly 1 is assembled as shown in FIG. 2, the first surface of the first substrate 2 and the first surface of the second substrate 3 will face each other, and the spacer part 4 will be positioned between the first substrate 2 and the second substrate 3 and the recess 7 together with first surfaces of the substrates 2 and 3 form a measuring cell 7a. The measuring cell 7a will be positioned in such a manner that the analyte sensors of the first substrate 2 as well as the analyte sensors 6 of the second substrate 3 are in fluid contact with the measuring cell 7a. Accordingly, the recess 7 in combination with the substrates 2, 3 define a measuring cell 7a in which a fluid sample may be accommodated. When a fluid sample is positioned in the measuring cell 7a each of the analyte sensors 6 will thereby be in contact with the sample and each of the analyte sensors 6 is accordingly capable of measuring relevant parameters of the sample.

Although the measuring cell 7a may have various different shapes, e.g. s-shape or bulging, it is preferred that the measuring cell 7a is as straight and even as possible to facilitate cleaning and avoid places were impurities may settle. Moreover, if the measuring cell 7a is straight and even, the lesser volume is required for the measuring cell 7a.

The measuring cell provides a volume of about 25-45 µl. The dimensions of the spacer are within the ranges: length 20-60 mm, width 5-20 mm, and thickness 0.2-0.6 mm.

Each of the analyte sensors 6 is connected to an associated electrical contact point 5c. The electrical contact points 5c may be connected to an analyzer via a suitable wiring. Thereby information regarding the measurement performed by an analyte sensor 6 may be transferred to the analyzer via an associated electrical contact point 5c, and the analyzer may then perform the necessary analysis of the measurement.

Since the electrical contact points 5c of the first substrate 2 and the electrical contact points 5c of the second substrate 3 face in the same direction, it is possible to access each of the electrical contact points 5c from the same side, thereby facilitating the connection to the analyzer and, thus, transfer of measurement information.

FIG. 2 is a perspective view of the assembled sensor assembly 1 of FIG. 1. It is clear from FIG. 2 that it is very easy to access each of the electrical contact points 5c of both substrates simultaneously.

As illustrated in FIG. 1 and FIG. 2 the sensor assembly 1 is basically constructed with three layers consisting of a first substrate 2, a spacer 4, and a second substrate 3. The first substrate 2 is equipped with analyte sensors on the first surface (not visible in FIG. 1), and the second surface with electric contact points 5c for establishing electric contact to an analyzer. In this illustrated preferred embodiment the first substrate 2 is further equipped with holes for an oxygen sensor 50, and reference electrode 51. The second substrate 3 is equipped with an inlet port 52 and an outlet port 53 for a fluid sample.

It is to be understood that the above description of the first and second substrates 2, 3 relates to specific embodiments, and that the inlet port 52 and the outlet port 53 may be placed in the first substrate 2, or the inlet port 52 may be placed in the first substrate 2 and the outlet port 53 in the second substrate 3 or vice versa. Moreover, the holes for oxygen sensor 50 and reference electrode 51 may be excluded or only one of them may be present, depending on the intended specific use of the sensor assembly. Furthermore, the substrates 2, 3 may be equipped with openings for other purposes if required.

The dimensions of the first and second substrate and the spacer, and thus, the dimension of the sensor assembly may be adapted depending on the intended use. However, in the disclosed embodiment the first substrate has dimensions within the ranges: length about 20-60 mm, width about 5-20 mm, and thickness about 0.3-0.8 mm.

The second substrate has dimensions within the ranges: length about 20-60 mm, width about 5-40 mm, and thickness 0.3-0.8 mm. The width of the second substrate 3 is somewhat larger than the width of the first substrate 2. This is due to the fact that for some preferred embodiments it is preferred that the first surface of the second substrate 3 projects over the edges of the spacer 4 and first substrate 2 in the sensor assembly 1. In this way it is possible to place the electric contact points 5c on the first surface of the second substrate in such a manner that the electric contact points 5c are accessible for external connecting means, e.g. pins on a contact element. The contact points 5c is, then, located on the part of the first surface of the second substrate that projects over the edges of the spacer 4 and the first substrate 2. Hereby, the contact points 5c on the first and second surface are available from one side, which makes it much simpler to establish electric contact between the contact points and a contact element connected to an analyzer unit.

The analyte sensors 6 comprises analyte sensors for measuring $pCO_2$, $pO_2$, pH, $Na^+$, $K^+$, $Ca^{2+}$, $Cl^-$, $Mg^{++}$, $Ca^{++}$, and additional analyte sensors may be present if required or desired e.g. analyte sensors measuring lactate, creatinine, and urea. Parameters like bilirubin and hemoglobin values, such as $FO_2Hb$, FCOHb, FMetHb, FHHb and FHbF may be measured in an additional module.

FIG. 3 is an exploded view of the sensor assembly 1 of FIG. 1 enclosed in a substantially closed housing 8 formed from a first housing part 8a and a second housing part 8b. Thereby the housing with the sensor assembly 1 of FIG. 3 forms a unit with facilitated handling properties.

Also enclosed by the housing 8 are a reference electrode 9 and a liquid chamber 10. During storage liquid is confined to the liquid chamber 10 due to valve element 11, and thereby the reference electrode 9 is kept dry. When it is intended to use the sensor assembly 1 the valve element 11 is operated to allow liquid to pass from the liquid chamber 10 to the reference electrode 9. This will be described in further detail below with reference to FIGS. 4 and 5.

FIG. 4 is an exploded view of the liquid chamber 10, which is shown in FIG. 3. The mutual position of the valve element 11, the liquid chamber 10 and the housing 8 appears from FIG. 4.

FIG. 5 is a cross sectional view of the liquid chamber 10 of FIG. 4 with the valve element 11 positioned therein. Initially and during storage the valve element 11 is positioned relatively to the liquid chamber 10 in such a manner that a lower part 11a of the valve element 11 abuts a downwards opening 12 of the liquid chamber 10, thereby sealing the liquid chamber 10 in a lower direction, and an upper part 11b of the valve element 11 abuts an upper opening 13 of the liquid chamber 10, thereby sealing the liquid chamber 10 in an upwards direction. Accordingly, liquid will be confined to the liquid chamber 10.

When it is desired to use the sensor assembly, the valve element 11 is pushed in a downward direction, i.e. towards the position shown in FIG. 5. Thereby liquid is allowed to flow from the liquid chamber 10 towards a reference electrode (not shown).

The liquid contained in the liquid chamber 10 is preferably a reference electrolyte which is required in order to allow the reference electrode to operate properly. However, during storage it is desirable to store the reference electrode under dry conditions in order to prevent, or at least reduce, degradation of the analyte sensors in the sensor assembly, which may occur if reference liquid leaks into the measuring cell and gets in contact with the analyte sensors. It is therefore an advantage that the valve element 11 is not operated to allow the reference electrolyte to get into contact with the reference electrode until it is intended to use the sensor assembly.

FIG. 6 is an exploded view of a conditioning unit 14 for storing and conditioning a sensor housing 8 with a sensor assembly 1. The sensor housing 8 shown in FIG. 6 is identical to the sensor housing 1 of FIG. 3.

The conditioning unit 14 comprises a first compartment 15 for accommodating the sensor housing 8 with the sensor assembly 1, and a second compartment 16 for containing a valve arrangement 19 with a liquid chamber 19a. The first compartment 15 is sealed by means of sealing cap 11 that serves to keep the sensor assembly 1 in a fixed position and moisture and gas tight foil 18. Additionally the first compartment 15 may comprise a siccative to absorb optional undesired moisture. The first compartment 15 is capable of storing the sensor assembly 1 functional for several years under dry or semidry conditions.

During storage the first compartment 15 and the second compartment 16 are mutually sealed, thereby confining liquid in liquid chamber 19a to the second compartment 16 and keeping the first compartment 15, and thereby the sensor assembly inside the sensor housing 8, under dry conditions.

Approximately two to twenty four hours before it is intended to use a new sensor assembly in an analyzer conditioning liquid is forced into the sensor assembly by activating the valve arrangement 19. This is done by twisting the second compartment 16 in relation to the first compartment 15. As a result of the twisting, the conditioning liquid is squeezed out of the liquid chamber 19a in the valve arrangement 19 and into the sensor assembly 1 in the first compartment. The device for obtaining the squeezing force on the chamber 19a in the valve arrangement 19 is e.g. a spring or an eccentric device located in the second compartment or a simple by pushing mechanism. Another way of activating the valve arrangement 19 may be by pushing the first compartment 15 and the second compartment 16 towards each other. A fluid connection between the sensor assembly in the sensor housing 8 stored in the first compartment 15 and the liquid chamber 19a is then established. Accordingly, liquid is allowed to flow from the liquid chamber 19a into the first compartment 15, and thereby into the sensor assembly in the sensor housing 8. This will cause the sensor assembly to be conditioned, i.e. it will be ready for use after a suitable time interval has elapsed. The liquid is conditioning liquid adapted for conditioning sensors before use and may easily be produced by a skilled person.

Accordingly with the conditioning unit 14, it is possible to store the sensor assembly under dry conditions in the first compartment 15, and it is possible to ensure conditioning of the sensor assembly when desired, thereby providing a sensor assembly which is ready for use at a specified time. Thereby downtime in relation to replacement of a used sensor assembly in an analyzer is minimized because the new sensor assembly may be conditioned while the sensor assembly to be replaced is still operating in the analyzer.

As it will be self-evident from the above and the following explanation, the sensor assembly and the conditioning unit forms a fully integrated system for delivering a fully functioning sensor assembly to an analyzer that is easy to use and where unproductive time is minimized. Thus, a sensor assembly that may be delivered ready-to-use to an analyzer is provided.

The conditioning unit 14 for storing and conditioning the sensor assembly not only stores the sensor assembly, but also makes it possible to condition the sensor assembly before use. In this manner the sensor assembly is instantly ready for use when transferred from the conditioning unit to the analyzer in which the sensor assembly is designed to operate. This feature provides a major advantage in operating the analyzer, as it is no longer necessary to condition the sensor assembly in the analyzer. Therefore, the analyzer may be utilized more effectively as the time previously spent on conditioning the sensor assembly in the analyzer is no longer required. The conditioning of the analyte sensors is required in order to make the analyte sensors function satisfactory. During the conditioning the sensor elements are wetted with a conditioning liquid to activate the analyte sensors. However, from the moment when the analyte sensors are wetted or conditioned they will start to break down, and the remaining lifetime of the analyte sensors is hereafter limited.

Consequently, when the sensor assembly in the conditioning unit is about to be used in an analyzer, the conditioning of the analyte sensors in the sensor assembly is activated (in the above-described embodiment the conditioning process is activated by twisting the second compartment in relation to the first compartment, however, other activation mechanism is also possible). When the conditioning has been activated the conditioning unit is placed untouched for about two to twenty four hours before the foil and sealing cap is removed and the sensor assembly is placed in an analyzer wherein the analyte sensors and reference electrode are connected to the analyzer via the electrical contact points. Due to the conditioning in the conditioning unit the sensor assembly is substantially operational when it is placed in the analyzer.

FIG. 7 shows a sensor assembly 1 comprising a housing 8. The housing is designed to fit in a holder 20 of an analyzer (not shown). The holder 20 comprises a hollow 21 for receiving the housing 8 and connecting holes 22 for transferring a sample between the analyzer and the sensor assembly 1.

Both the housing 8 and the receiving hollow 21 has a unique shape ensuring that the housing 8 is placed correctly in the holder 20. In the holder 20 the inlet hole 52 and the outlet hole 53 of the sensor assembly 1 communicates with corresponding connecting holes 22 in the holder in such a way that a fluid sample may be delivered to the sensor assembly 1 via the inlet hole 52 and leave the sensor assembly via outlet hole 53.

FIG. 8 shows the housing 8 with the sensor assembly 1 and a contact element 23 with pins 24 to provide electrical contact between the electric contact points on the sensor assembly 1 and an analyzer.

FIG. 9 shows a cross sectional view of the contact element 23 attached to the housing 8. Electrical contact is established between the electrical contact points 5c on the sensor assembly 1 and the pins 24 in the electrical contact element 23. The housing 8 is fixed in holder 20 of an analyzer.

As seen in FIGS. 8 and 9 a contact element 23 is placed in the housing 8 and connects to the contact points 5c on the sensor assembly 1. The contact element 23 transfers the information from the electrical contact points 5 and in doing so also transfers information from the analyte sensors 6 to processing in the analyzer, e.g. a blood analyzer.

The invention claimed is:

1. A sensor assembly comprising:
a first electronic wiring substrate having a first surface and a second surface and at least two analyte sensors formed on the first surface thereof, the at least two analyte sensors being connected with electrical contact points,
a second electronic wiring substrate having a first surface and a second surface and at least two analyte sensors formed on the first surface thereof, the at least two analyte sensors being connected with electrical contact points, and
a spacer having a through-going recess with a first opening and a second opening,
wherein the first substrate, the second substrate and the spacer are arranged in a layered structure, where the first surface of the first substrate closes the first opening of the spacer and the first surface of the second substrate closes the second opening of the spacer, thereby forming a measuring cell in which all the analyte sensors on the first surface of the first substrate face the measuring cell through the first opening of the spacer and wherein all the analyte sensors on the first surface of the second substrate face the measuring cell through the second opening of the spacer, the measuring cell having a shape allowing fluid flow through the measuring cell to be substantially linear.

2. The sensor assembly according to claim 1, wherein the electrical contact points of the first substrate are arranged on the second surface of the first substrate and wherein the electrical contact points of the second substrate are arranged on the first surface of the second substrate.

3. The sensor assembly according to claim 2, wherein the analyte sensors and the contact points of the second substrate are connected via wiring extending from the sensors through the substrate to the second surface thereof and from the second surface through the substrate to the contact points.

4. The sensor assembly according to claim 3, wherein a part of the second substrate extends beyond the first substrate.

5. The sensor assembly according to claim 4, wherein the electrical contact points of the second substrate are positioned on the extending part.

6. The sensor assembly according to claim 1, wherein at least one of the substrates is made from a ceramic material.

7. The sensor assembly according to claim 1, wherein the measuring cell has inlet and outlet ports, the ports being formed in the first substrate.

8. The sensor assembly according to claim 1, wherein the measuring cell has inlet and outlet ports, the ports being formed in the second substrate.

9. The sensor assembly according to claim 1, wherein the sensor assembly is at least substantially enclosed in a housing.

10. The sensor assembly according to claim 1, wherein the analyte sensors are blood parameter sensors.

11. A sensor assembly comprising:
a first electronic wiring substrate having a first surface and a second surface and at least two analyte sensors formed on the first surface thereof, the at least two analyte sensors being connected with electrical contact points,
a second electronic wiring substrate having a first surface and a second surface and at least two analyte sensors formed on the first surface thereof, the at least two analyte sensors being connected with electrical contact points, and
a spacer having a through-going recess with a first opening and a second opening,
wherein the first substrate, the second substrate and the spacer are arranged in a layered structure, wherein the first opening of the spacer is closed by the at least two analyte sensors formed on the first surface of the first substrate and by portions of the first surface of the first substrate and wherein the second opening of the spacer is closed by the at least two analyte sensors formed on the first surface of the second substrate and by portions of the second substrate, thereby forming a measuring cell in which all the analyte sensors on the first surface of the first substrate face the measuring cell through the first opening of the spacer and wherein all the analyte sensors on the first surface of the second substrate face the measuring cell through the second opening of the spacer, the measuring cell having a shape allowing fluid flow through the measuring cell to be substantially linear.

12. The sensor assembly according to claim 11, wherein the first and second openings of the spacer extend the length of a flow path defined by the measuring cell.

13. The sensor assembly according to claim 11, wherein the first and second openings are the only openings of the spacer that define a portion of the measuring cell.

* * * * *

UNITED STATES PATENT AND TRADEMARK OFFICE
CERTIFICATE OF CORRECTION

PATENT NO. : 8,728,288 B2  
APPLICATION NO. : 12/081997  
DATED : May 20, 2014  
INVENTOR(S) : Aas et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1395 days.

Signed and Sealed this
Twenty-eighth Day of July, 2015

Michelle K. Lee
*Director of the United States Patent and Trademark Office*